United States Patent [19]

Kurmeier et al.

[11] Patent Number: 5,164,114
[45] Date of Patent: Nov. 17, 1992

[54] ETHYNE DERIVATIVES

[75] Inventors: Hans A. Kurmeier, Seeheim-Jugenheim; Volker Reiffenrath, Rossdorf; Eike Poetsch, Mühtal; Joachim Krause, Dieburg; Georg Weber, Erzhausen, all of Fed. Rep. of Germany

[73] Assignee: Merck Patent Gesellschaft Mit Beschraenkter Haftung, Darmstadt, Fed. Rep. of Germany

[21] Appl. No.: 283,449

[22] PCT Filed: Mar. 25, 1988

[86] PCT No.: PCT/EP88/00246
§ 371 Date: Nov. 25, 1988
§ 102(e) Date: Nov. 25, 1988

[87] PCT Pub. No.: WO88/07516
PCT Pub. Date: Oct. 6, 1988

[30] Foreign Application Priority Data

Mar. 27, 1987 [DE] Fed. Rep. of Germany ....... 3710069

[51] Int. Cl.$^5$ ................. C09K 19/34; C09K 19/30; C07D 239/02; C07C 19/08
[52] U.S. Cl. ................. 252/299.61; 252/299.63; 252/299.66; 252/299.67; 252/299.01; 570/129; 544/298; 546/340
[58] Field of Search .................. 252/299.61, 299.63, 252/299.66, 299.67, 299.01; 570/129; 544/298, 340

[56] References Cited

U.S. PATENT DOCUMENTS

| | | | |
|---|---|---|---|
| 3,925,482 | 12/1975 | Jacques | 252/299.01 |
| 4,410,283 | 10/1983 | Dubois et al. | 252/299.64 |
| 4,754,051 | 6/1988 | Sasaki et al. | 252/299.67 |
| 4,778,620 | 10/1988 | Goto et al. | 252/299.63 |
| 4,788,363 | 11/1988 | Takatsu et al. | 252/299.63 |
| 4,814,516 | 3/1989 | Takeuchi et al. | 252/299.01 |
| 4,816,180 | 3/1989 | Goto et al. | 252/299.63 |
| 4,839,091 | 6/1989 | Goto et al. | 252/299.63 |
| 4,921,632 | 5/1990 | Nakamura et al. | 252/299.01 |
| 4,925,590 | 5/1990 | Reiffenrath et al. | 252/299.61 |
| 4,961,874 | 10/1990 | Takeuchi et al. | 252/299.6 |
| 5,068,053 | 11/1991 | Reiffenrath et al. | 252/299.61 |

FOREIGN PATENT DOCUMENTS 01301639 12/1989 Japan ................. 252/299.6

OTHER PUBLICATIONS

Titov, V. et al. CA89 (23) 197123j, 1978.

Primary Examiner—Robert L. Stoll
Assistant Examiner—C. Harris
Attorney, Agent, or Firm—Millen, White, Zelano and Branigan

[57] ABSTRACT

Ethyne derivatives of the formula I $$R^1-(A^1-Z^1)_m-A^3-C\equiv C-A^4-(Z^2-A^2)_n-R^2 \qquad I$$

wherein $R^1$, $A^1$, $Z^1$, m, $A^3$, $A^4$, $_2Z^2$ and n have the meaning given in Claim 1 and $R^2$ is $-OCF_3$, $-OC_2F_4H$ or $-OC_2F_5$, are suitable as components of liquid crystal phases.

12 Claims, No Drawings

ETHYNE DERIVATIVES

The invention relates to ethyne derivatives of the formula I

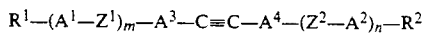

$$R^1-(A^1-Z^1)_m-A^3-C\equiv C-A^4-(Z^2-A^2)_n-R^2 \qquad I$$

wherein $R^1$ is an alkyl or alkenyl radical having 1 to 15 C atoms which is unsubstituted, monosubstituted by —CN or at least monosubstituted by halogen, it also being possible for one or more $CH_2$ groups in these radicals in each case independently of one another to be replaced by —O—, —S—, —CO—, —O—CO—, —O—COO—, —CO—O— or —C≡C— such that heteroatoms are not linked directly to one another, H, halogen, —CN or —NCS, $R^2$ is —$OCF_3$, —$OC_2F_5$ or —$OC_2F_4H$, $A^1$ and $A^2$ in each case independently of one another are a
 a) 1,4-phenylene radical, wherein one or more CH groups can also be replaced by N,
 b) trans-1,4-cyclohexylene radical, wherein one or two non-adjacent $CH_2$ groups can also be replaced by —O— and/or —S—,
 c) radical from the group comprising 1,4-cyclohexenylene, 1,4-cyclohexadienylene or 1,4-bicyclo-(2.2.2)-octylene,
  it being possible for the radicals a) and b) to be substituted once or more than once by halogen, cyano and/or $CH_3$, $Z^1$ and $Z^2$ in each case independently of one another are —CO—O—, —O—CO—, —$CH_2$O—, —O$CH_2$—, —$CH_2CH_2$—, —C≡C— or a single bond, m and n in each case independently of one another are 0 or 1, and $A^3$ and $A^4$ in each case independently of one another are a
 a) 1,4-phenylene or 4,4'-biphenylene radical, wherein one or more CH groups can also be replaced by N,
 b) trans-1,4-cyclohexylene radical,
 c) radical from the group comprising 1,4-cyclohexenylene, 1,4-cyclohexadienylene or 1,4-bicyclo(2.2.2)octylene,
  it being possible for the radicals a) and b) to be substituted once or more than once by halogen, cyano and/or $CH_3$, with the proviso that in at least one of the groups $A^3$ or $A^4$ at least one CH group is replaced by N and/or at least one of the groups $A^3$ and $A^4$ is trans-1,4-cyclohexylene or 1,4-bicyclo(2.2.2)octylene and/or at least one of the groups $A^1$, $A^2$, $A^3$ and $A^4$ is 1,4-cyclohexenylene or 1,4-cyclohexadienylene.

For simplicity, in the following text Phe is an unsubstituted 1,4-phenylene group, PheX is a substituted 1,4-phenylene group (where X is halogen, CN and/or $CH_3$), Cyc is a 1,4-cyclohexylene group, Che is a 1,4-cyclohexenylene group, Cha is a 1,4-cyclohexadienylene group, Dio is a 1,3-dioxane-2,5-diyl group, Dit is a 1,3-dithiane-2,5-diyl group, Pyd is a pyridine-2,5-diyl group, Pyr is a pyrimidine-2,5-diyl group, Pyz is a pyrazine-2,5-diyl group, Pyn is a pyridazine-3,6-diyl group, Bco is a 1,4-bicyclo(2.2.2)octylene group and Biphe is a 4,4'-biphenylyl group, wherein one or more CH groups can also be replaced by N.

The compounds of the formula I can be used as components of liquid crystal phases, in particular for displays based on the principle of the twisted cell, on the guest-host effect, on the effect of deformation of orientated phases or on the effect of dynamic scattering.

Similar compounds are known, for example, from European Patent 111,695-A, for displays which operate by the two-frequency method.

The invention was based on the object of discovering new stable liquid crystal or mesogenic compounds which are suitable as components of liquid crystal phases. This object was achieved by providing the compounds of the formula I.

It has been found that the compounds of the formula I are outstandingly suitable as components of liquid crystal phases In particular, these compounds are distinguished by a positive dielectric anisotropy and a high birefringence.

The compounds of the formula I are thus preferably suitable for use as components of liquid crystal phases for SBE or OMI applications.

Surprisingly, it has been found that the addition of compounds of the formula I gives liquid crystal phases with wide nematic ranges.

By providing the compounds of the formula I, the range of liquid crystal substances which are suitable from various technological aspects for the preparation of nematic mixtures is also quite generally widened considerably.

The compounds of the formula I have a wide range of applications. Depending on the selection of the substituents, these compounds can be used as the base materials from which liquid crystal phases are predominantly composed; however, it is also possible to add compounds of the formula I to liquid crystal base materials from other classes of compounds, for example in order to optimize the dielectric and/or optical anisotropy of such a dielectric.

The compounds of the formula I are furthermore suitable as intermediates for the preparation of other substances which can be used as constituents of liquid crystal phases.

The compounds of the formula I are colorless in the pure state and form liquid crystal mesophases in a temperature range which is favorably placed for electro-optical use. They are very stable towards chemicals, heat and light.

The invention thus relates to the compounds of the formula I and the use of these compounds as components of liquid crystal phases. The invention furthermore relates to liquid crystal phases containing at least one compound of the formula I and liquid crystal display elements containing such phases.

$R^1$, $A^1$, $Z^1$, m, $A^3$, $A^4$, $Z^2$, $A^2$, n and $R^2$ above and below have the meaning given, unless expressly indicated otherwise.

The compounds of the formula I accordingly include compounds of the part formulae Ia (with two rings), Ib to Ie (with three rings) and If to Ii (with four rings):

| | |
|---|---|
| $R^1-A^3-C\equiv C-A^4-R^2$ | Ia |
| $R^1-A^3-C\equiv C-A^4-A^2-R^2$ | Ib |
| $R^1-A^3-C\equiv C-A^4-Z^2-A^2-R^2$ | Ic |
| $R^1-A^1-A^3-C\equiv C-A^4-R^2$ | Id |
| $R^1-A^1-Z^1-A^3-C\equiv C-A^4-R^2$ | Ie |
| $R^1-A^1-Z^1-A^3-C\equiv C-A^4-Z^2-A^2-R^2$ | If |

-continued

| | |
|---|---|
| $R^1-A^1-A^3-C\equiv C-A^4-Z^2-A^2-R^2$ | Ig |
| $R^1-A^1-Z^1-A^3-C\equiv C-A^4-A^2-R^2$ | Ih |
| $R^1-A^1-A^3-C\equiv C-A^4-A^2-R^2$ | Ii |

The preferred compounds of the part formula Ia include those of the part formulae Iaa to Ian:

| | |
|---|---|
| $R^1-Cyc-C\equiv C-Phe-R^2$ | Iaa |
| $R^1-Cyc-C\equiv C-PheX-R^2$ | Iab |
| $R^1-Che-C\equiv C-Phe-R^2$ | Iac |
| $R^1-Cha-C\equiv C-Phe-R^2$ | Iad |
| $R^1-Pyd-C\equiv C-Phe-R^2$ | Iae |
| $R^1-Pyr-C\equiv C-Phe-R^2$ | Iaf |
| $R^1-Pyz-C\equiv C-Phe-R^2$ | Iag |
| $R^1-Pyn-C\equiv C-Phe-R^2$ | Iah |
| $R^1-Bco-C\equiv C-Phe-R^2$ | Iai |
| $R^1-Cyc-C\equiv C-Biphe-R^2$ | Iak |
| $R^1-Pyd-C\equiv C-Biphe-R^2$ | Ial |
| $R^1-Che-C\equiv C-PheX-R^2$ | Iam |
| $R^1-Cha-C\equiv C-PheX-R^2$ | Ian |

Of these, those of the formulae Iaa, Iab, Iac, Iae, Iaf, Iak and Iam are particularly preferred.

The preferred compounds of the part formulae Ib, Ic, Id and Ie include those of the part formulae I1 to I22:

| | |
|---|---|
| $R^1-Cyc-C\equiv C-A^4-Z^2-A^2-R^2$ | I1 |
| $R^1-Che-C\equiv C-A^4-Z^2-A^2-R^2$ | I2 |
| $R^1-Cha-C\equiv C-A^4-Z^2-A^2-R^2$ | I3 |
| $R^1-Bco-C\equiv C-A^4-Z^2-A^2-R^2$ | I4 |
| $R^1-Pyd-C\equiv C-A^4-Z^2-A^2-R^2$ | I5 |
| $R^1-Pyr-C\equiv C-A^4-Z^2-A^2-R^2$ | I6 |
| $R^1-Pyz-C\equiv C-A^4-Z^2-A^2-R^2$ | I7 |
| $R^1-Pyn-C\equiv C-A^4-Z^2-A^2-R^2$ | I8 |
| $R^1-A^3-C\equiv C-Cyc-Z^2-A^2-R^2$ | I9 |
| $R^1-A^3-C\equiv C-Che-Z^2-A^2-R^2$ | I10 |
| $R^1-A^3-C\equiv C-Cha-Z^2-A^2-R^2$ | I11 |
| $R^1-A^3-C\equiv C-Bco-Z^2-A^2-R^2$ | I12 |
| $R^1-Biphe-C\equiv C-A^4-Z^2-A^2-R^2$ | I13 |
| $R^1-A^3-C\equiv C-Biphe-Z^2-A^2-R^2$ | I14 |
| $R^1-A^3-C\equiv C-Pyd-Z^2-A^2-R^2$ | I15 |
| $R^1-A^3-C\equiv C-Pyr-Z^2-A^2-R^2$ | I16 |
| $R^1-A^3-C\equiv C-Pyz-Z^2-A^2-R^2$ | I17 |
| $R^1-A^3-C\equiv C-Pyn-Z^2-A^2-R^2$ | I18 |
| $R^1-A^3-C\equiv C-A^4-Z^2-Che-R^2$ | I19 |
| $R^1-A^3-C\equiv C-A^4-Z^2-Cha-R^2$ | I20 |
| $R^1-Che-Z^1-A^3-C\equiv C-A^4-R^2$ | I21 |
| $R^1-Cha-Z^1-A^3-C\equiv C-A^4-R^2$ | I22 |

Of these, those of the formulae I1, I2, I5, I6, I9, I10, I13, I14, I15, I18, I19 and I20 are particularly preferred.

The preferred compounds of the part formulae If, Ig, Ih and Ii include those of the part formulae I23 to I33:

| | |
|---|---|
| $R^1-A^1-Z^1-Cyc-C\equiv C-A^4-Z^2-A^2-R^2$ | I23 |
| $R^1-A^1-Z^1-Che-C\equiv C-A^4-Z^2-A^2-R^2$ | I24 |
| $R^1-A^1-Z^1-Cha-C\equiv C-A^4-Z^2-A^2-R^2$ | I25 |
| $R^1-A^1-Z^1-Bco-C\equiv C-A^4-Z^2-A^2-R^2$ | I26 |
| $R^1-A^1-Z^1-Pyd-C\equiv C-A^4-Z^2-A^2-R^2$ | I27 |
| $R^1-A^1-Z^1-Pyr-C\equiv C-A^4-Z^2-A^2-R^2$ | I28 |
| $R^1-A^1-Z^1-Pyz-C\equiv C-A^4-Z^2-A^2-R^2$ | I29 |
| $R^1-A^1-Z^1-Pyn-C\equiv C-A^4-Z^2-A^2-R^2$ | I30 |
| $R^1-A^1-Z^1-Biphe-C\equiv C-A^4-Z^2-A^2-R^2$ | I31 |
| $R^1-Che-Z^1-A^3-C\equiv C-A^4-Z^2-A^2-R^2$ | I32 |
| $R^1-Cha-Z^1-A^3-C\equiv C-A^4-Z^2-A^2-R^2$ | I33 |

In the formulae above and below, $R^1$ is preferably alkyl, alkoxy or another oxaalkyl group.

Alkenyl groups, or alkyl groups which are monosubstituted by —CN are furthermore preferred for $R^1$.

Alkyl groups substituted by halogen are likewise preferred.

Halogen is fluorine, chlorine or bromine. Substitution by fluorine or chlorine is preferred.

$R^1$ furthermore is also halogen, —CN or —NCS.

$A^1$ and $A^2$ are preferably Cyc, PheX or Phe, and furthermore also Che or Cha. PheX preferably denotes monosubstitution by F, Cl or CN.

$A^1$ and $A^2$ are furthermore preferably a Bco, Pyd, Dio or Pyr group.

$A^3$ and $A^4$ are preferably Cyc, Pyd, Pyr, Che, Phe or Cha, and furthermore preferably Bco, PheX, Biphe, Pyn or Pyz.

In at least one of the groups $A^3$ or $A^4$ at least one CH group is replaced by N and/or at least one of the groups $A^3$ and $A^4$ is Cyc or Bco and/or at least one of the groups $A^1$, $A^2$, $A^3$ or $A^4$ is Che or Cha. Preferably, only one of the groups $A^3$ or $A^4$ is a pyridine, cyclohexyl or pyrimidine radical.

m and n in each case independently of one another are 0 or 1. Preferably, $m+n=1$.

$Z^1$ and $Z^2$ are preferably single bonds, —CO—O— or —O—CO—. —CH$_2$CH$_2$—, —C≡C—, —OCH$_2$— or —CH$_2$O— are of second preference.

If $R^1$ is an alkyl radical in which one ("alkoxy" or "oxaalkyl") or two ("alkoxyalkoxy" or "dioxaalkyl") non-adjacent CH$_2$ groups can also be replaced by O atoms, it can be straight-chain or branched. Preferably, it is straight-chain, has 2, 3, 4, 5, 6 or 7 C atoms and is accordingly preferably ethyl, propyl, butyl, pentyl, hexyl, heptyl, ethoxy, propoxy, butoxy, pentoxy, hexoxy, heptoxy, 2- oxapropyl (=methoxymethyl), 2- (=ethoxymethyl) or 3- oxabutyl (=2-methoxyethyl), 2-, 3- or 4-oxapentyl, 2- 3-, 4- or 5-oxahexyl, 2-, 3-, 4-, 5- or 6-oxaheptyl, and furthermore methyl, octyl, nonyl, decyl, undecyl, dodecyl, tridecyl, tetradecyl, pentadecyl, methoxy, octoxy, nonoxy, decoxy, undecoxy, dodecoxy, tridecoxy, tetradecoxy, pentadecoxy, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl, 1,3-dioxabutyl (=methoxymethoxy), 1,3-, 1,4- or 2,4-dioxapentyl, 1,3-, 1,4-, 1,5-, 2,4-, 2,5- or 3,5-dioxahexyl or 1,3-, 1,4-, 1,5-, 1,6-, 2,4-, 2,5-, 2,6-, 3,5-, 3,6- or 4,6-dioxaheptyl.

End group substituents in which a CH$_2$ group is replaced by a —C≡C— group are also particularly preferred.

Compounds of the formula I with a branched end group substituent $R^1$ may occasionally be of importance because of a better solubility in the customary liquid crystal base materials, but in particular as chiral doping substances, if they are optically active.

Branched groups of this type as a rule contain not more than one chain branching. Preferred branched radicals are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, 2-octyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy (=2-octyloxy), 2-oxa-3-methylbutyl, 3-oxa-4-methylpentyl, 4-methylhexyl, 2-nonyl, 2-decyl, 2-dodecyl, 6-methyloctoxy, 6-methyloctanoyloxy, 5-methylheptyloxy-carbonyl, 2-methylbutyryloxy, 3-methylvaleryloxy, 4-methylhexanoyloxy, 2-chloropropionyloxy, 2-chloro-3-methylbutyryloxy, 2-chloro-4-methylvaleryloxy, 2-chloro-3-methylvaleryloxy, 2-methyl-3-oxapentyl and 2-methyl-3-oxahexyl.

In the case of compounds with branched end group substituents, formula I includes both the optical antipodes and racemates as well as mixtures thereof.

Of the compounds of the formula I and sub-formulae thereof, those in which at least one of the radicals contained therein has one of the preferred meanings given are preferred.

The 1,4-cyclohexenylene group preferably has the following structures:

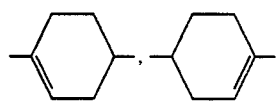

The 1,4-cyclohexadienylene group preferably has the following structure:

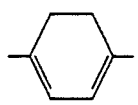

Particularly preferred smaller groups of compounds are those of the formulae 1 to 43:

| | |
|---|---|
| Alkyl—Cyc—C≡C—Phe—OCF₃ | 1 |
| Alkyl—Cyc—C≡C—PheX—OCF₃ | 2 |
| Alkyl—Che—C≡C—Phe—OCF₃ | 3 |
| Alkyl—Cha—C≡C—Phe—OCF₃ | 4 |
| CF₃O—Phe—C≡C—Pyd—Alkyl | 5 |
| Alkyl—Cyc—C≡C—Phe—OC₂F₄H | 6 |
| Alkyl—Cyc—C≡C—Phe—OC₂F₅ | 7 |
| Alkyl—Pyd—C≡C—Phe—OC₂F₄H | 8 |
| Alkyl—Pyd—C≡C—Phe—OC₂F₅ | 9 |
| Alkyl—Cyc—Cyc—C≡C—Phe—OC₂F₄H | 10 |
| Alkyl—Cyc—Cyc—C≡C—Phe—OC₂F₅ | 11 |
| Alkyl—Phe—Cyc—C≡C—Phe—OC₂F₄H | 12 |
| Alkyl—Phe—Cyc—C≡C—Phe—OC₂F₅ | 13 |
| Alkyl—Phe—Pyd—C≡C—Phe—OC₂F₄H | 14 |
| Alkyl—Phe—Pyd—C≡C—Phe—OC₂F₅ | 15 |
| Alkyl—Cyc—C≡C—Biphe—OCF₃ | 16 |
| Alkoxy—Pyd—C≡C—Phe—OCF₃ | 17 |
| Alkyl—Bco—C≡C—Phe—OCF₃ | 18 |
| CH₃O—Phe—C≡C—Pyn—Alkyl | 19 |
| Alkyl—Cyc—C≡C—Phe—COO—Phe—OCF₃ | 20 |
| Alkyl—Che—C≡C—Phe—OCO—Phe—OCF₃ | 21 |
| R¹—Cha—Phe—C≡C—Phe—OCF₃ | 22 |
| R¹—Cyc—CH₂CH₂—Cyc—C≡C—Phe—OCF₃ | 23 |
| R¹—Phe—Pyd—C≡C—Phe—OCF₃ | 24 |
| R¹—Che—Phe—C≡C—Phe—OCF₃ | 25 |
| R¹—Pyr—C≡C—Phe—OCO—Phe—OCF₃ | 26 |
| R¹—Phe—Phe—C≡C—Cyc—Phe—OCF₃ | 27 |
| R¹—Phe—COO—Phe—C≡C—Pyd—Phe—OCF₃ | 28 |
| R¹—Phe—OCH₂—Phe—C≡C—Cyc—Phe—OCF₃ | 29 |
| R¹—Cyc—Cyc—C≡C—Pyn—Phe—OCF₃ | 30 |
| Alkyl—Che—Phe—C≡C—Phe—OCF₃ | 31 |
| R¹—Che—Phe—C≡C—Phe—Phe—OCF₃ | 32 |
| R¹—Phe—Bco—C≡C—Phe—COO—Phe—OCF₃ | 33 |
| R¹—Cyc—Cha—C≡C—Phe—Phe—OCF₃ | 34 |
| R¹—Cyc—Cyc—C≡C—Pyr—Phe—OCF₃ | 35 |
| R¹—Phe—Phe—C≡C—Pyz—Phe—OCF₃ | 36 |
| R¹—Phe—Che—C≡C—Phe—Phe—OCF₃ | 37 |
| Alkyl—Cyc—C≡C—Cyc—C≡C—Phe—OCF₃ | 38 |
| Alkyl—Cyc—Cyc—C≡C—Phe—OCF₃ | 39 |
| Alkyl—Phe—Cyc—C≡C—Phe—OCF₃ | 40 |
| Alkyl—Pyr—C≡C—Phe—OCF₃ | 41 |
| Alkyl—Pyr—C≡C—Phe—OC₂F₄H | 42 |
| Alkyl—Pyr—C≡C—Phe—OC₂F₅ | 43 |

Compounds of the formula I in which one of the groups $A^1$, $A^2$, $A^3$ and $A^4$ is a 2,3-dihalogeno-1,4-phenylene group are also preferred. In these compounds, halogen is fluorine, chlorine or bromine. Fluorine is the preferred substituent.

The compounds of the formula I are prepared by methods which are known per se, such as are described in the literature (for example in the standard works, such as Houben-Weyl, Methoden der Organischen Chemie (Methods of Organic Chemistry), Georg-Thieme-Verlag, Stuttgart), and in particular under reaction conditions which are known and suitable for the reactions mentioned. In these reactions, it is also possible to utilize variants which are known per se and are not mentioned here in more detail.

If desired, the starting substances can also be formed in situ so that they are not isolated from the reaction mixture but are immediately reacted further to give the compounds of the formula I.

The compounds of the formula I with a triple bond can thus be prepared by brominating the corresponding stilbenes and then subjecting the products to dehydrohalogenation. In this process, variants of this reaction which are known per se and are not mentioned in more detail can be used.

The stilbenes can be prepared by reaction of a 4-substituted benzaldehyde with a corresponding phosphorus ylide by the method of Wittig or by reaction of a 4-substituted phenylethylene with a corresponding bromobenzene derivative by the method of Heck.

Another possibility for the preparation of the C—C triple bond comprises a procedure in which a compound which otherwise corresponds to the formula I but contains a —CH₂—CO— group instead of the —C≡C— bond is either reacted with an inorganic acid chloride and the —CH₂—CCl₂— group then formed is dehydrohalogenated in the presence of a base, or is reacted with semicarbazide and selenium dioxide. The triple bond is then introduced in the presence of methyllithium, while heating.

There is furthermore the possibility of converting a corresponding benzil derivative into the ethyne derivative with hydrazine and then with HgO.

Compounds of the formula I can also be prepared via coupling of alkynyl-zinc compounds with aryl halides by a method analogous to that described by A. O. King, E. Negishi, F. J. Villani and A. Silveira in J.Org.Chem. 43 (1978) 358.

Compounds of the formula I can also be prepared via the Fritsch-Buttenberg-Wiechell rearrangement (Ann. 279, 319, 327, 332, 1894), in which 1,1-diaryl-2-halogenoethylenes are rearranged into diarylacetylenes in the presence of strong bases.

Compounds of the formula I can furthermore be prepared from 4-substituted phenyl- or cyclohexylacetylenes and aryl halides in the presence of a palladium catalyst, for example bis(triphenylphosphine)-palladium-(II) chloride, and copper(I) iodide (described in Synthesis (1980) 627 or Tetrahedron Letters 27 (1986) 1171).

The corresponding trifluoromethoxybenzene derivatives are preferably used as starting compounds in this reaction. The trifluoromethoxy group can be introduced, for example, by reaction of a corresponding phenol derivative with anhydrous hydrofluoric acid in an autoclave at 0° in carbon tetrachloride, or the known 4-trifluoromethoxybenzaldehyde or 4-tetrafluoroethoxybenzaldehyde is used as the starting substance.

Compounds of the formula I are furthermore obtainable by adding a compound of the formula HX (hydrogen fluoride, chloride, bromide or cyanide) onto a corresponding cyclohexene derivative.

This addition reaction is effected, for example, in the presence of an inert solvent, for example a halogenated hydrocarbon, such as $CH_2Cl_2$ os $CHCl_3$, a nitrile, such as acetonitrile, or an amide, such as dimethylformamide (DMF) at temperatures between about $-10°$ and $+150°$ under pressures between about 1 and 100 bar. It may be advantageous to add catalysts, for example an HCN addition reaction can be catalyzed by addition of palladium bis-[2,3-0-isopropylidene-2,3-dihydroxy-1,4-bis-(diphenylphosphino)-butane].

Esters of the formula I (—CO—O— or —O—CO— group in $R^1$ and/or $Z^2$ and/or $Z^1$=—CO—O— or —O—CO—) can also be obtained by esterification of corresponding carboxylic acids (or their reactive derivatives) with alcohols or phenols (or their reactive derivatives). The esterification of acids with alcohols or phenols can also be carried out with DCC/DMAP.

Suitable reactive derivatives of the carboxylic acids mentioned are, in particular, the acid halides, above all the chlorides and bromides, and furthermore the anhydrides, for example also mixed anhydrides, azides or esters, in particular alkyl esters having 1-4 C atoms in the alkyl group.

Possible reactive derivatives of the alcohols or phenols mentioned are, in particular, the corresponding metal alcoholates or phenolates. In these, the metal is preferably an alkali metal, such as Na or K.

Dioxane derivatives or dithiane derivatives of the formula 1 (wherein one of the groups $A^1$ and/or $A^2$ is a 1,3-dioxane-2,5-diyl group or 1,3-dithiane-2,5-diyl group) are advantageously prepared by reaction of a corresponding aldehyde (or one of its reactive derivatives) with a corresponding 1,3-diol (or one of its reactive derivatives) or a corresponding 1,3-dithiol, preferably in the presence of an inert solvent, such as benzene or toluene, and/or a catalyst, for example a strong acid, such as sulfuric acid or benzene- or p-toluenesulfonic acid, at temperatures between about 20° and about 150°, preferably between 80° and 120°. Suitable reactive derivatives of the starting substances are above all acetals.

The aldehydes and 1,3-diols or 1,3-dithiols mentioned and their reactive derivatives are known in some cases, and in some cases they can be prepared without difficulty by standard methods of organic chemistry, from compounds which are known from the literature. For example, the aldehydes are obtainable by oxidation of corresponding alcohols or by reduction of corresponding carboxylic acids or their derivatives, the diols are obtainable by reduction of corresponding diesters and the dithiols are obtainable by reaction of corresponding dihalides with NaSH.

To prepare nitriles of the formula I (wherein $R^1$ is CN and/or wherein $A^3$ and/or $A^4$ and/or $A^1$ and/or $A^2$ is substituted by at least one CN group), corresponding acid amides can be dehydrated. The amides are obtainable, for example, from the corresponding esters or acid halides by reaction with ammonia. Suitable dehydrating agents are, for example, inorganic acid chlorides, such as $SOCl_2$, $PCl_3$, $PCl_5$, $POCl_3$, $SO_2Cl_2$, or $COCl_2$, and furthermore $P_2O_5$, $P_2S_5$ or $AlCl_3$ (for example as a double compound with NaCl), and aromatic sulfonic acids and sulfonic acid halides. This reaction can be carried out in the presence or absence of an inert solvent at temperatures between about 0° and 150°; examples of possible solvents are bases, such as pyridine or triethylamine, aromatic hydrocarbons, such as benzene, toluene or xylene, or amides, such as DMF.

To prepare the abovementioned nitriles of the formula I, it is also possible to react corresponding acid halides, preferably the chlorides, with sulfamide, advantageously in an inert solvent, such as tetramethylene sulfone, at temperatures between about 80° and 150°, preferably at 120°. After customary working up, the nitriles can be isolated directly.

Ethers of the formula I (wherein $R^1$ is an alkyl group wherein one or two $CH_2$ groups can be replaced by 0 atoms, and/or wherein $Z^2$ and/or $Z^1$ is an —$OCH_2$— or a —$CH_2O$— group) are obtainable by etherification of corresponding phenols, the hydroxy compound advantageously first being converted into a corresponding metal derivative, for example into the corresponding alkali metal alcoholate or alkali metal phenolate by treatment with NaH, $NaNH_2$, NaOH, KOH, $Na_2CO_3$ or $K_2CO_3$. This metal derivative can then be reacted with the corresponding alkyl halide or sulfonate or dialkyl sulfate, advantageously in an inert solvent, such as acetone, 1,2-dimethoxyethane, DMF or dimethyl sulfoxide, or else an excess of aqueous or aqueous-alcoholic NaOH or KOH, at temperatures between about 20° and 100°.

To prepare compounds of the formula I which are substituted laterally by halogen, in principle all the methods which are known for the preparation of such compounds can be used. The synthesis variants required can be deduced by the expert by routine methods.

The liquid crystal phases according to the invention consist of 2 to 15, preferably 3 to 12, components, at least one of which is a compound of the formula I. The other constituents are preferably selected from the nematic or nematogenic substances, in particular the known substances, from the classes of azoxybenzenes, benzylideneanilines, biphenyls, terphenyls, phenyl or cyclohexyl benzoates, phenyl or cyclohexyl cyclohexanecarboxylates, phenylcyclohexanes, cyclohexylbiphenyls, cyclohexylcyclohexanes, cyclohexylnaphthalenes, 1,4-bis-cyclohexylbenzenes, 4,4'-bis-cyclohexylbiphenyls, phenyl- or cyclophexylpyrimidines (sic), phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, optionally halogenated stilbenes, benzyl phenyl ethers and substituted cinnamic acids.

The most important compounds which are possible constituents of such liquid crystal phases can be characterized by the formula IV $R^6$-L-G-E-$R^7$    IV wherein L and E are each a carbo- or heterocyclic ring system from the group formed by 1,4-disubstituted benzene and cyclohexane rings, 4,4'-disubstituted biphenyl, phenylcyclohexane and cyclohexylcyclohexane systems, 2,5-disubstituted pyrimidine and 1,3-dioxane rings, 2,6-disubstituted naphthalene, di- and tetrahydronaphthalene, quinazoline and tetrahydroquinazoline, G is

| G | —CH=CH— | —N(O)=N— |
|---|---|---|
| | —CH=CY— | —CH=N(O)— |
| | —C≡C— | —$CH_2$—$CH_2$— |
| | —CO—O— | —$CH_2$—O— |
| | —CO—S— | —$CH_2$—S— |

-continued

| —CH=N— | —COO—Phe—COO— | or a C—C single bond,

Y is halogen, preferably chlorine, or —CN and $R^6$ and $R^7$ are alkyl, alkoxy, alkanoyloxy or alkoxycarbonyloxy having up to 18, preferably up to 8, carbon atoms, or one of these radicals is also CN, NC, $NO_2$, $CF_3$, F, Cl or Br.

In most of these compounds, $R^6$ and $R^7$ differ from one another, one of these radicals usually being an alkyl or alkoxy group. Other variants of the envisaged substituents are also also (sic) customary. Many such substances or mixtures thereof are commercially available. All these substances are obtainable by methods which are known from the literature.

The phases according to the invention contain about 0.1 to 99, preferably 10 to 95% of one or more compounds of the formula I. Liquid crystal phases according to the invention which contain 0.1-40, preferably 0.5-30%, of one or more compounds of the formula I are furthermore preferred.

The compounds of the formula I can also be used as components of smectic or chirally tilted smectic liquid crystal phases. These phases are preferably chirally tilted smectic liquid crystal phases, the achiral base mixture of which contains, in addition to compounds of the formula I, at least one other component with negative or relatively low positive dielectric anisotropy. This (these) other component(s) of the achiral base mixture can make up to 1 to 50%, preferably 10 to 25%, of the base mixture.

The phases according to the invention are prepared in the manner which is customary per se. As a rule, the components are dissolved in one another, advantageously at elevated temperature.

The liquid crystal phases according to the invention can be modified by suitable additives such that they can be used in all the types of liquid crystal display elements which have been disclosed to date.

Such additives are known to the expert and are described in detail in the literature. For example, it is possible to add conductive salts, preferably ethyldimethyl-dodecyl-ammonium 4-hexyloxybenzoate, tetrabutylammonium tetraphenylboranate or complex salts of crown ethers (compare, for example, I. Haller et al., Mol. Cryst. Liq. Cryst. Volume 24, pages 249-258 (1973)) to improve the conductivity, dichroic dyestuffs to prepare colored guest-host systems or substances for modifying the dielectric anisotropy, the viscosity and/or the alignment of the nematic phases. Such substances are described, for example, in German Offenlegungsschrift 2,209,127, 2,240,864, 2,321,632, 2,338,281, 2,450,088, 2,637,430, 2,853,728 and 2,902,177.

The following examples are intended to illustrate the invention without limiting it. M.=melting point, C.=clear point. Percentage data above and below are percentages by weight; all the temperatures are stated in degrees Celsius. "Customary working up" means: water is added, the mixture is extracted with methylene chloride, the organic phase is separated off, dried and evaporated, and the product is purified by crystallization and/or chromatography.

EXAMPLE 1

0.2 m of 4-trifluoromethoxybenzaldehyde and 0.2 m of 2-methyl-5-methylpyridine are heated at 200° together with 3 g of zinc chloride for 2 days. The course of the reaction can be monitored with the aid of thin layer chromatography. When the reaction has ended, excess starting material is distilled off and the residue is purified by crystallization or chromatography.

0.1 m of the stilbene derivative thus obtained is brominated with 0.1 m of $Br_2$ in 200 ml of glacial acetic acid at room temperature, while stirring. When the addition has ended, the mixture is briefly heated to the boiling point. The glacial acetic acid is then evaporated off and 200 ml of tert.-butanol are added to the residue. 0.4 m of potassium tert.-butanolate are added to this mixture at room temperature and the mixture is subsequently heated at the boiling point for 3 hours. After cooling, water is added and the mixture is extracted with ether. Working up of the organic phase and purification by chromatography gives 1-(4-trifluoromethoxyphenyl)-2-(5-methyl-pyridin-2-yl)-acetylene.

The following compounds are prepared analogously:

1-(4-trifluoromethoxyphenyl)-2-(5-ethyl-pyridin-2-yl)-acetylene 1-(4-trifluoromethoxyphenyl)-2-(5-propyl-pyridin-2-yl)-acetylene 1-(4-trifluoromethoxyphenyl)-2-(5-butyl-pyridin-2-yl)-acetylene 1-(4-trifluoromethoxyphenyl)-2-(5-pentylpyridin-2-yl)-acetylene 1-(4-trifluoromethoxyphenyl)-2-(5-hexyl-pyridin-2-yl)-acetylene 1-(4-trifluoromethoxyphenyl)-2-(5-heptyl-pyridin-2-yl)-acetylene 1-(4-trifluoromethoxyphenyl)-2-(5-octyl-pyridin-2-yl)-acetylene 1-(4-trifluromethoxyphenyl)-2-(5-methoxy-pyridin-2-yl)-acetylene 1-]1-(4-trifluoromethoxyphenyl)-2-(5-ethoxy-pyridin-2-yl)-acetylene 1-(4-trifluoromethoxyphenyl)-2-(5-propoxy-pyridin-2-yl)-acetylene 1-(4-trifluoromethoxyphenyl)-2-(5-butoxy-pyridin-2-yl)-acetylene 1-(4-trifluoromethoxyphenyl)-2-(5-pentyloxy-pyridin-2-yl)-acetylene 1-(4-trifluoromethoxyphenyl)-2-(5-hexyloxy-pyridin-2-yl)-acetylene 1-(4-trifluoromethoxyphenyl)-2-(5-heptyloxy-pyridin-2-yl)-acetylene 1-(4-trifluoromethoxyphenyl)-2-(5-octyloxy-pyridin-2-yl)-acetylene

EXAMPLE 2

A solution of 0.2 m of potassium tert.-butanolate in 150 ml of tetrahydrofuran is added to 0.2 m of trans-4-(trans-4-propylcyclohexyl)-cyclohexylmethyl-triphenylphosphonium iodide and 0.2 m of 4-trifluoromethoxybenzaldehyde together in 250 ml of tetrahydrofuran at 0°-5° in a Wittig reaction. After the mixture has been stirred at room temperature for 1 hour, it is neutralized with dilute HCl, the phosphonium oxide is filtered off and the filtrate is worked up by extraction. Purification by crystallization gives the corresponding stilbene product.

0.1 m of this stilbene compound is brominated with 0.1 m of $Br_2$ in 100 ml of acetonitrile at 0°-5°. The product which has precipitated is filtered off and dried. The dibromide is then heated under reflux with 0.2 m of potassium tert.-butanolate and 150 ml of tert.-butanol for 3 hours. After cooling, the mixture is poured onto water and the product is taken up in petroleum ether.

Working up by extraction and purification by crystallization gives 1-[trans-4-(trans-4-propylcyclohexyl)cyclohexyl]-2-(4-trifluoromethoxyphenyl)-acetylene.

The following compounds are prepared analogously:
1-[trans-4-(trans-4-methylcyclohexyl)cyclohexyl]-2-(4-trifluoromethoxyphenyl)-acetylene
1-[trans-4-(trans-4-ethylcyclohexyl)cyclohexyl]-2-(4-trifluoromethoxyphenyl)-acetylene
1-[trans-4-(trans-4-butylcyclohexyl)cyclohexyl]-2-(4-trifluoromethoxyphenyl)-acetylene
1-[trans-4-(trans-4-pentylcyclohexyl)cyclohexyl]-2-(4-trifluoromethoxyphenyl)-acetylene
1-[trans-4-(trans-4-hexylcyclohexyl)cyclohexyl]-2-(4-trifluoromethoxyphenyl)-acetylene
1-[trans-4-(trans-4-heptylcyclohexyl)cyclohexyl]-2-(4-trifluoromethoxyphenyl)-acetylene
1-[trans-4-(trans-4-octylcyclohexyl)cyclohexyl]-2-(4-trifluoromethoxyphenyl)-acetylene
1-(trans-4-propylcyclohexyl)-2-(4-trifluoromethoxyphenyl)-acetylene
1-(trans-4-ethylcyclohexyl)-2-(4-trifluoromethoxyphenyl)-acetylene
1-(trans-4-butylcyclohexyl)-2-(4-trifluoromethoxyphenyl)-acetylene
1-(trans-4-pentylcyclohexyl)-2-(4-trifluoromethoxyphenyl)-acetylene
1-(trans-4-hexylcyclohexyl)-2-(4-trifluoromethoxyphenyl)-acetylene
1-(trans-4-heptylcyclohexyl)-2-(4-trifluoromethoxyphenyl)-acetylene
1-(trans-4-octylcyclohexyl)-2-(4-trifluoromethoxyphenyl)-acetylene
1-[trans-4-(4-propylphenyl)cyclohexyl]-2-(4-trifluoromethoxyphenyl)-acetylene
1-[trans-4-(4-ethylphenyl)cyclohexyl]-2-(4-trifluoromethoxyphenyl)-acetylene
1-[trans-4-(4-butylphenyl)cyclohexyl]-2-(4-trifluoromethoxyphenyl)-acetylene
1-[trans-4-(4-pentylphenyl)cyclohexyl]-2-(4-trifluoromethoxyphenyl)-acetylene
1-[trans-4-(4-hexylphenyl)cyclohexyl]-2-(4-trifluoromethoxyphenyl)-acetylene
1-[trans-4-(4-heptylphenyl)cyclohexyl]-2-(4-trifluoromethoxyphenyl)-acetylene
1-[trans-4-(4-octylphenyl)cyclohexyl]-2-(4-trifluoromethoxyphenyl)-acetylene

EXAMPLE 3

Analogously to Example 2, the corresponding 1-(trans-4-propylcyclohexyl)-2-[4-(1,1,2,2-tetrafluoroethoxy)phenyl]-acetylene is obtained from 4-(1,1,2,2-tetrafluoroethoxy)benzaldehyde and trans-4-propylcyclohexylmethylphosphonium iodide.

The following compounds are prepared analogously:
1-(trans-4-ethylcyclohexyl)-2-[4-(1,1,2,2-tetrafluoroethoxy)phenyl]-acetylene
1-(trans-4-methylcyclohexyl)-2-[4-(1,1,2,2-tetrafluoroethoxy)phenyl]-acetylene
1-(trans-4-butylcyclohexyl)-2-[4-(1,1,2,2-tetrafluoroethoxy)phenyl]-acetylene
1-(trans-4-pentylcyclohexyl)-2-[4-(1,1,2,2-tetrafluoroethoxy)phenyl]-acetylene
1(trans-4-hexylcyclohexyl)-2-[4-(1,1,2,2-tetrafluoroethoxy)phenyl]-acetylene
1-(trans-4-heptylcyclohexyl)-2-[4-(1,1,2,2-tetrafluoroethoxy)phenyl]-acetylene
1-(trans-4-octylcyclohexyl)-2-[4-(1,1,2,2-tetrafluoroethoxy)phenyl]-acetylene
1-[trans-4-(trans-4-propylcyclohexyl)cyclohexyl]-2-[4-(1,1,2,2-tetrafluoroethoxy)phenyl]-acetylene
1-[trans-4-(trans-4-methylcyclohexyl)cyclohexyl]-2-[4-(1,1,2,2-tetrafluoroethoxy)phenyl]-acetylene
1-[trans-4-(trans-4-butylcyclohexyl)cyclohexyl]-2-[4-(1,1,2,2-tetrafluoroethoxy)phenyl]-acetylene
1-[trans-4-(trans-4-pentylcyclohexyl)cyclohexyl]-2-[4(1,1,2,2-tetrafluoroethoxy)phenyl]-acetylene
1-[trans-4-(trans-4-hexylcyclohexyl)cyclohexyl]-2-[4(1,1,2,2-tetrafluoroethoxy)phenyl]-acetylene
1-[trans-4-(trans-4-heptylcyclohexyl)cyclohexyl]-2-[4-(1,1,2,2-tetrafluoroethoxy)phenyl]-acetylene
1-[trans-4-(trans-4-octylcyclohexyl)cyclohexyl]-2-[ 4-(1,1,2,2-tetrafluoroethoxy)phenyl]-acetylene
1-[trans-4-(4-propylphenyl)cyclohexyl]-2-[4-(1,1,2,2-tetrafluoroethoxy)phenyl]-acetylene
1-[trans-4-(4-methylphenyl)cyclohexyl]-2-[4-(1,1,2,2-tetrafluoroethoxy)phenyl]-acetylene
1-[trans-4-(4-butylphenyl)cyclohexyl]-2-[4-(1,1,2,2-tetrafluoroethoxy)phenyl]-acetylene
1-[trans-4-(4-pentylphenyl)cyclohexyl]-2-[4 (1,1,2,2-tetrafluoroethoxy)phenyl]-acetylene
1-[trans-4-(4-hexylphenyl)cyclohexyl]-2-[4-(1,1,2,2-tetrafluoroethoxy)phenyl]-acetylene
1-[trans-4-(4-heptylphenyl)cyclohexyl]-2-[4-(1,1,2,2-tetrafluoroethoxy)phenyl]-acetylene
1-[trans-4-(4-octylphenyl)cyclohexyl]-2-[4-(1,1,2,2-tetrafluoroethoxy)phenyl]-acetylene

EXAMPLE 4

Analogously to Example 1, the corresponding 1-[4-(1,1,2,2-tetrafluoroethoxy)phenyl]-2-(5-methyl-pyridin-2-yl)-acetylene is obtained from 4-(1,1,2,2-tetrafluoroethoxy)benzaldehyde and 2-methyl-5-methylpyridine.

The following compounds are prepared analogously:
1-[4-(1,1,2,2-tetrafluoroethoxy)phenyl]-2-(5-ethyl-pyridin-2-yl)-acetylene
1-[4-(1,1,2,2-tetrafluoroethoxy)phenyl]-2-(5-propyl-pyridin-2-yl)-acetylene
1-[4-(1,1,2,2-tetrafluoroethoxy)phenyl]-2-(5-butyl-pyridin-2-yl)-acetylene
1-[4-(1,1,2,2-tetrafluoroethoxy)phenyl]-2-(5-pentyl-pyridin-2-yl)-acetylene
1-[4-(1,1,2,2-tetrafluoroethoxy)phenyl]-2-(5-hexyl-pyridin-2-yl)-acetylene
1-[4-(1,1,2,2-tetrafluoroethoxy)phenyl]-2-(5-heptyl-pyridin-2-yl)-acetylene
1-[4-(1,1,2,2-tetrafluoroethoxy)phenyl]-2-(5-octyl-pyridin-2-yl)-acetylene
1-[4-(1,1,2,2-tetrafluoroethoxy)phenyl]-2-(5-methoxy-pyridin-2-yl)-acetylene
1-[4-(1,1,2,2-tetrafluoroethoxy)phenyl]-2-(5-ethoxy-pyridin-2-yl)-acetylene
1-[4-(1,1,2,2-tetrafluoroethoxy)phenyl]-2-(5-propoxy-pyridin-2-yl)-acetylene
1-[4-(1,1,2,2-tetrafluoroethoxy)phenyl]-2-(5-butoxy-pyridin-2-yl)-acetylene
1-[4-(1,1,2,2-tetrafluoroethoxy)phenyl]-2-(5-pentyloxy-pyridin-2-yl)-acetylene
1-[4-(1,1,2,2-tetrafluoroethoxy)phenyl]-2-(5-hexyloxy-pyridin-2-yl)-acetylene
1-[4-(1,1,2,2-tetrafluoroethoxy)phenyl]-2-(5-heptyloxy-pyridin-2-yl)-acetylene
1-[4-(1,1,2,2-tetrafluoroethoxy)phenyl]-2-(5-octyloxy-pyridin-2-yl)-acetylene

EXAMPLE 5

Starting from 4-trifluoromethoxybenzaldehyde, the corresponding cinnamic acid is obtained by reaction (analogously to Organic Syntheses, page 327) with malonic acid. This cinnamic acid is converted into the nitrile by reaction with 1. SOCl$_2$, 2. NH3 and 3. POCl$_3$.

The nitrile is converted into an amidine by a method analogous to that described by P. E. Fanta et al. in J. Am. Chem. Soc., Volume 78, 1434, and this is converted into 1-(4-trifluoromethoxyphenyl)-2-(5-pentyl-pyrimidin-2-yl)-ethene with a sodium salt of 2-pentylmalonalde.

This stilbene derivative is brominated in acetonitrile at 0°–5° and the product is then dehydrobrominated with potassium tert.-butanolate in tert.-butanol. Customary working up and purification gives 1-(4-trifluoromethoxyphenyl)-2-(5-pentyl-pyrimidin-2-yl)-ethyne.

The following compounds are prepared analogously:
1-(4-trifluoromethoxyphenyl)-2-(5-ethyl-pyrimidin-2-yl)-ethyne
1-(4-trifluoromethoxyphenyl)-2-(5-methyl-pyrimidin-2-yl)-ethyne
1-(4-trifluoromethoxyphenyl)-2-(5-propyl-pyrimidin-2-yl)-ethyne
1-(4-trifluoromethoxyphenyl)-2-(5-butyl-pyrimidin-2-yl)-ethyne
1-(4-trifluoromethoxyphenyl)-2-(5-pentyl-pyrimidin-2-yl)-ethyne
1-(4-trifluoromethoxyphenyl)-2-(5-hexyl-pyrimidin-2-yl)-ethyne
1-(4-trifluoromethoxyphenyl)-2-(5-heptyl-pyrimidin-2-yl)-ethyne
1-(4-trifluoromethoxyphenyl)-2-(5-octyl-pyrimidin-2-yl)-ethyne
1-[4-(1,1,2,2-tetrafluoroethoxy)phenyl]-2-(5-pentyl-pyrimidin-2-yl)-ethyne
1-[4-(1,1,2,2-tetrafluoroethoxy)phenyl]-2-(5-ethyl-pyrimidin-2-yl)-ethyne
1-[4-(1,1,2,2-tetrafluoroethoxy)phenyl]-2-(5-methyl-pyrimidin-2-yl)-ethyne
1-[4-(1,1,2,2-tetrafluoroethoxy)phenyl]-2-(5-propyl-pyrimidin-2-yl)-ethyne
1-[4-(1,1,2,2-tetrafluoroethoxy)phenyl]-2-(5-butyl-pyrimidin-2-yl)-ethyne
1-[4-(1,1,2,2-tetrafluoroethoxy)phenyl]-2-(5-hexyl-pyrimidin-2-yl)-ethyne
1-[4-(1,1,2,2-tetrafluoroethoxy)phenyl]-2-(5-heptyl-pyrimidin-2-yl)-ethyne
1-[4-(1,1,2,2-tetrafluoroethoxy)phenyl]-2-(5-octyl-pyrimidin-2-yl)-ethyne

EXAMPLE A

A liquid crystal phase is prepared from
9% of r-1-cyano-cis-4-(trans-4-propylcyclohexyl)-1-propyl-cyclohexane,
5% of r-1-cyano-1-propyl-cis-4-(4'-propylbiphenyl-4-yl)-cyclohexane,
26% of 2-fluoro-4-ethyl-4'-[2-(trans-4-propyl-cyclohexyl)-ethyl]-biphenyl,
25% of 2-fluoro-4-pentyl-4'-[2-(trans-4-propyl-cyclohexyl)ethyl]-biphenyl,
23% of 2-fluoro-4-ethyl-4'-[2-(trans-4-pentyl-cyclohexyl)-ethyl]-biphenyl,
5% of 4-(trans-4-propylcyclohexyl)-2'-fluoro-4'-(trans-4-propylcyclohexyl)-biphenyl and
7% of 1-(4-trifluoromethoxyphenyl)-2-(trans-4-ethyl-cyclohexyl)-acetylene.

We claim:

1. Ethyne derivatives of the formula I

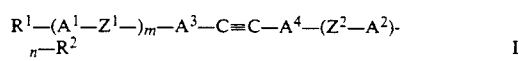

wherein
R$^1$ is an alkyl or alkenyl radical having 1 to 15 C atoms which is unsubstituted, monosubstituted by —CN or at least monosubstituted by halogen, it also being possible for one or more CH$_2$ groups in these radicals in each case independently of one another to be replaced by —O—, —S—, —CO—, —O—CO—, —O—COO—, —CO—O— or —C≡C— such that heteroatoms are not linked directly to one another, H, halogen, —CN or —NCS, R$^2$ is —OCF$_3$, —OC$_2$F$_5$ or —OC$_2$F$_4$H, A$^1$ and A$^2$ in each case independently of one another are a
a) 1,4-phenylene radical, wherein one or more CH groups can also be replaced by N,
b) trans-1,4-cyclohexylene radical, wherein one or two non-adjacent CH$_2$ groups can also be replaced by independently replaced by —O— or —S—,
c) radical from the group comprising 1,4-cyclohexenylene, 1,4-cyclohexadienylene or 1,4-bicyclo-(2.2.2)-octylene,
it being possible for the radicals a) and b) to be substituted once or more than once by halogen, cyano and/or CH$_3$, Z$^1$ and Z$^2$ in each case independently of one another are —CO—O—, —O—CO—, —CH$_2$O—, —OCH$_2$—, —CH$_2$CH$_2$—, —C≡C— or a single bond, m and n in each case independently of one another are 0 or 1, A$^3$ and A$^4$ in each case independently of one another are a
a) 1,4-phenylene or 4,4'-biphenylene radical, wherein one or more CH groups can also be replaced by N,
b) trans-1,4-cyclohexylene radical,
c) radical from the group comprising 1,4-cyclohexenylene, 1,4-cyclohexadienylene or 1,4-bicyclo(2.2.2)octylene,
it being possible for the radicals a) and b) to be substituted once or more than once by halogen, cyano and/or CH$_3$, with the proviso that in at least one of the groups A$^3$ or A$^4$ at least one CH group is replaced by N and/or at least one of the groups A$^3$ and A$^4$ is trans-1,4-cyclohexylene or 1,4-bicyclo(2.2.2)octylene and/or at least one of the groups A$^1$, A$^2$, A$^3$ and A$^4$ is 1,4-cyclohexenylene or 1,4-cyclohexadienylene.

2. Liquid crystal phase with at least two liquid crystal components, characterized in that it contains at least one compound of the formula I according to claim 1.

3. Liquid crystal display element, characterized in that it contains a liquid crystal phase according to claim 2.

4. An ethyne derivative of formula I

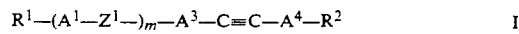

wherein
- $R^1$ is an alkyl or alkenyl radical having 1 to 15 C atoms which is unsubstituted, monosubstituted by —CN or substituted by at least one halogen atom, wherein one or more $CH_2$ groups in the radical independently of one another may be replaced by —O—, —S—, —CO—, —O—CO—, —O—COO—, —CO—O— or —C≡C— such that heteroatoms are not linked directly to one another,
- $R^2$ is —$OCF_3$, —$OC_2F_5$ or —$OC_2F_4H$,
- $A^1$ is
  - a) a trans-1,4-cyclohexylene radical, wherein one or two non-adjacent $CH_2$ groups can also be replaced by independently replaced by —O— or —S—, or
  - b) a radical from the group consisting of 1,4-cyclohexenylene, 1,4-cyclohexadienylene and 1,4-bicyclo-(2.2.2)-octylene,
- $Z^1$ is —CO—O—, —O—CO—, —$CH_2O$—, —$OCH_2$—, —$CH_2CH_2$—, —C≡C— or a single bond,
- m is 0 or 1,
- $A^4$ is a 1,4-phenylene or 4,4'-biphenylene radical, or such a radical independently substituted once or more than once by halogen CN or $CH_3$, and
- $A^3$ is trans-1,4-cyclohexylene.

5. An ethyne derivative of claim 4, wherein $R^1$ is alkyl, alkoxy, oxaalkyl or alkenyl.

6. An ethyne derivative of claim 4, wherein $A^1$ is trans-1,4-cyclohexylene.

7. An ethyne derivative of claim 6, wherein $Z^1$ is —$CH_2CH_2$— or a single bond.

8. An ethyne derivative of claim 4, wherein $A^4$ is 1,4-phenylene or 1,4-phenylene substituted by halogen.

9. An ethyne derivative of claim 4 of the formula alkyl—Cyc—C≡C—Phe—$OCF_3$, wherein Cyc is 1,4-cyclohexylene and Phe is 1,4-phenylene.

10. An ethyne derivative of claim 4 of the formula alkyl—Cyc—C≡C—PheX—$OCF_3$, wherein Cyc is 1,4-cyclohexylene and PheX is substituted 1,4-phenylene wherein X is halogen, CN, $CH_3$, or a combination thereof.

11. An ethyne derivative of claim 4 of the formula $R^1$—Cyc—$CH_2CH_2$—Cyc—C≡C—Phe—$OCF_3$, wherein Cyc is 1,4-cyclohexylene and Phe is 1,4-phenylene.

12. An ethyne derivative of claim 7 of the formula alkyl—Cyc—Cyc—C≡C—Phe—$OCF_3$, wherein Cyc is 1,4-cyclohexylene and Phe is 1,4-phenylene.

* * * * *